(12) United States Patent
Zhang et al.

(10) Patent No.: US 10,755,411 B2
(45) Date of Patent: Aug. 25, 2020

(54) METHOD AND APPARATUS FOR ANNOTATING MEDICAL IMAGE

(71) Applicant: BAIDU ONLINE NETWORK TECHNOLOGY (BEIJING) CO., LTD., Beijing (CN)

(72) Inventors: Shaoting Zhang, Beijing (CN); Weidong Zhang, Beijing (CN); Qi Duan, Beijing (CN)

(73) Assignee: BAIDU ONLINE NETWORK TECHNOLOGY (BEIJING) CO., LTD., Beijing (CN)

( * ) Notice: Subject to any disclaimer, the term of this patent is extended or adjusted under 35 U.S.C. 154(b) by 109 days.

(21) Appl. No.: 16/051,214

(22) Filed: Jul. 31, 2018

(65) Prior Publication Data

US 2019/0096060 A1 Mar. 28, 2019

(30) Foreign Application Priority Data

Sep. 27, 2017 (CN) .......................... 2017 1 0888651

(51) Int. Cl.
*G06T 7/00* (2017.01)
*A61B 6/03* (2006.01)

(52) U.S. Cl.
CPC .......... *G06T 7/0012* (2013.01); *G06T 7/0014* (2013.01); *A61B 6/032* (2013.01);
(Continued)

(58) Field of Classification Search
CPC ................. G06T 7/0012; G06T 7/0014; G06T 2207/20084; G06T 2207/30041;
(Continued)

(56) References Cited

U.S. PATENT DOCUMENTS

| 9,378,331 B2 * | 6/2016 | Reicher ................. G06F 19/321 |
| 10,354,049 B2 * | 7/2019 | Mabotuwana ......... G16H 15/00 |

(Continued)

FOREIGN PATENT DOCUMENTS

| CN | 107103187 A | 8/2017 |
| CN | 107203995 A | 9/2017 |

*Primary Examiner* — Brandon J Miller
(74) *Attorney, Agent, or Firm* — Marshall, Gerstein & Borun LLP

(57) ABSTRACT

An embodiment of the present disclosure discloses a method and apparatus for annotating a medical image. An embodiment of the method comprises: acquiring a to-be-annotated medical image; annotating classification information for the to-be-annotated medical image, wherein the classification information comprises a category of a diagnosis result and a grade of the diagnosis result corresponding to the medical image; processing the to-be-annotated medical image using a pre-trained lesion area detection model, framing a lesion area in the to-be-annotated medical image, and annotating a lesion type of the lesion area, to enable the to-be-annotated medical image to be annotated with the lesion area and the lesion type of the lesion area; and splitting the framed lesion area from the to-be-annotated medical image with the framed lesion area to form a split image of the to-be-annotated medical image, to enable the to-be-annotated medical image to be annotated with the split image.

23 Claims, 5 Drawing Sheets

(52) U.S. Cl.
CPC ............... *G06T 2207/10081* (2013.01); *G06T 2207/10088* (2013.01); *G06T 2207/20081* (2013.01); *G06T 2207/20084* (2013.01); *G06T 2207/30041* (2013.01); *G06T 2207/30061* (2013.01); *G06T 2207/30096* (2013.01)

(58) Field of Classification Search
CPC . G06T 2207/20081; G06T 2207/30061; G06T 2207/10088; G06T 2207/30096; G06T 2207/10081; A61B 6/032
See application file for complete search history.

(56) References Cited

U.S. PATENT DOCUMENTS

| | | | |
|---|---|---|---|
| 10,499,845 B2* | 12/2019 | Do | G06K 9/38 |
| 2015/0261915 A1* | 9/2015 | Yanagida | G06F 16/5866 |
| | | | 382/131 |
| 2016/0364526 A1 | 12/2016 | Reicher et al. | |
| 2017/0287134 A1* | 10/2017 | Abedini | G06K 9/622 |
| 2018/0060487 A1* | 3/2018 | Barkan | G06F 17/241 |
| 2018/0092696 A1* | 4/2018 | Qian | G06F 19/321 |

\* cited by examiner

METHOD AND APPARATUS FOR ANNOTATING MEDICAL IMAGE

CROSS-REFERENCE TO RELATED APPLICATION

This application is related to and claims priority from Chinese Application No. 201710888651.2, filed on Sep. 27, 2017 and entitled "Method and Apparatus for Annotating Medical Image," the entire disclosure of which is hereby incorporated by reference.

TECHNICAL FIELD

The present disclosure relates to the field of computer technology, specifically to the field of Internet technology, and more specifically to a method and apparatus for annotating a medical image.

BACKGROUND

In the existing technology, due to the particularity of a medical image, usually only a professionally trained doctor can accurately and reliably annotate a medical image. In the process of annotating a medical image, a doctor is usually required to manually determine a disease type, selecting a lesion area, delineating the lesion area, and the like. The doctor needs to spend a considerable amount of time and energy in this annotating process.

Furthermore, in order to realize the development of medical science in the fields such as deep learning and computer-aided diagnosis, collecting a considerable amount of annotated medical images is in urgent need. However, collecting a considerable amount of annotated medical images usually results in a lot of labor and time cost.

SUMMARY

An objective of an embodiment of the present disclosure is to provide an improved method and apparatus for annotating a medical image, in order to solve the technical problem mentioned in the foregoing Background section.

In a first aspect, an embodiment of the present disclosure provides a method for annotating a medical image, including: acquiring a to-be-annotated medical image; annotating classification information for the to-be-annotated medical image, wherein the classification information includes a category of a diagnosis result and a grade of the diagnosis result corresponding to the medical image; processing the to-be-annotated medical image using a pre-trained lesion area detection model, framing a lesion area in the to-be-annotated medical image, and annotating a lesion type of the lesion area, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and splitting the framed lesion area from the to-be-annotated medical image with the framed lesion area to form a split image of the to-be-annotated medical image, to enable the to-be-annotated medical image to be annotated with the split image.

In some embodiments, the annotating classification information for the to-be-annotated medical image includes: processing the to-be-annotated medical image using a pre-trained image classification model to output the classification information of the to-be-annotated medical image, wherein the image classification model is used for annotating the classification information for the medical image.

In some embodiments, the splitting the framed lesion area from the to-be-annotated medical image with the framed lesion area to form a split image of the to-be-annotated medical image includes: processing the to-be-annotated medical image with the framed lesion area using a pre-trained lesion area splitting model to output the split image of the framed lesion area in the to-be-annotated medical image, wherein the lesion area splitting model is used for obtaining the split image of the lesion area by splitting the medical image with the framed lesion area.

In some embodiments, the method further includes training an image classification model. The training an image classification model includes: acquiring a first medical image training set, the first medical image training set including a plurality of medical images and the classification information annotated on each of the medical images; and obtaining the image classification model by training, using a convolutional neural network based on the first medical image training set.

In some embodiments, the method further includes training the lesion area detection model. The training the lesion area detection model includes: acquiring a second medical image training set, the second medical image training set including a plurality of medical images, lesion areas and lesion types of the lesion areas annotated on each of the medical images; and obtaining the lesion area detection model by training, using a convolutional neural network based on the second medical image training set.

In some embodiments, the method further includes training the lesion area splitting model. The training the lesion area splitting model includes: acquiring a third medical image training set, the third medical image training set including a plurality of medical images with framed lesion areas and a split image of the lesion areas of the medical images with the framed lesion areas; and obtaining the lesion area splitting model by training, using a convolutional neural network based on the third medical image training set.

In some embodiments, after the processing the to-be-annotated medical image using a pre-trained lesion area detection model, framing a lesion area in the to-be-annotated medical image, and annotating the lesion type of the lesion area, the method further includes: outputting the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct; and saving the annotated lesion area and the lesion type of the lesion area in the to-be-annotated medical image, if the annotated lesion area and the lesion type of the lesion area in the to-be-annotated medical image are correct; or receiving and saving a lesion area and a lesion type of the lesion area in the to-be-annotated medical image re-annotated by the user, if the annotated lesion area and the lesion type of the lesion area in the to-be-annotated medical image are not correct.

In some embodiments, before the outputting the split image of the framed lesion area in the to-be-annotated medical image, the method further includes: forming a pre-split area in the lesion area of the to-be-annotated medical image using the lesion area splitting model, and outputting the pre-split area to a client terminal, to enable a user to slightly adjust the pre-split area; and receiving and saving the pre-split area slightly adjusted by the user.

In some embodiments, the method further includes: adding the to-be-annotated medical image and the classification information of the to-be-annotated medical image to the first medical image training set to retrain the image classification model.

In some embodiments, the method further includes: adding the to-be-annotated medical image, and the annotated lesion area and the lesion type of the lesion areas in the to-be-annotated medical image to the second medical image training set to retrain the lesion area detection model.

In some embodiments, the method further includes: adding the to-be-annotated medical image with the framed lesion area and the split image of the to-be-annotated medical image to the third medical image training set to retrain the lesion area splitting model.

In a second aspect, the present disclosure provides an apparatus for annotating a medical image. The apparatus includes: an acquisition unit configured to acquire a to-be-annotated medical image; a first annotation unit configured to annotate classification information for the to-be-annotated medical image, wherein the classification information includes a category of a diagnosis result and a grade of the diagnosis result corresponding to the medical image; a second annotation unit configured to process the to-be-annotated medical image using a pre-trained lesion area detection model, frame a lesion area in the to-be-annotated medical image, and annotate a lesion type of the lesion area, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and a third annotation unit configured to split the framed lesion area from the to-be-annotated medical image with the framed lesion area to form a split image of the to-be-annotated medical image, to enable the to-be-annotated medical image to be annotated with the split image.

In some embodiments, the first annotation unit is further configured to: process the to-be-annotated medical image using a pre-trained image classification model to output the classification information of the to-be-annotated medical image, wherein the image classification model is used for annotating a category of a diagnosis result and a grade of the diagnosis result for the medical image.

In some embodiments, the third annotation unit is further configured to: process the to-be-annotated medical image with the framed lesion area using a pre-trained lesion area splitting model to output the split image of the framed lesion area in the to-be-annotated medical image, wherein the lesion area splitting model is used for obtaining the split image of the lesion area by splitting the medical image with the framed lesion area.

In some embodiments, the apparatus further includes an image classification model training unit. The image classification model training unit includes: a first acquisition module configured to acquire a first medical image training set, the first medical image training set including a plurality of medical images and the classification information annotated on each of the medical images; and a first training module configured to obtain the image classification model by training, using a convolutional neural network based on the first medical image training set.

In some embodiments, the apparatus further includes: a lesion area detection model training unit.

The lesion area detection model training unit includes a second acquisition module configured to acquire a second medical image training set, the second medical image training set including a plurality of medical images, lesion areas and lesion types of the lesion areas annotated on each of the medical images; and a second training unit configured to obtain the lesion area detection model by training, using a convolutional neural network based on the second medical image training set.

In some embodiments, the apparatus further includes a lesion area splitting model training unit. The lesion area splitting model training unit includes: a third acquisition module configured to acquire a third medical image training set, the third medical image training set including a plurality of medical images with framed lesion areas and a split image of the lesion areas of the medical images with the framed lesion areas; and a third training module configured to obtain the lesion area splitting model by training, using a convolutional neural network based on the third medical image training set.

In some embodiments, the second annotation unit is further configured to: output the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct; and save the annotated lesion area and the lesion type of the lesion area in the to-be-annotated medical image, if the annotated lesion area, and the lesion type of the lesion area in the to-be-annotated medical image are correct; or receive and save a lesion area and a lesion type of the lesion area in the to-be-annotated medical image re-annotated by the user, if the annotated lesion area, and the lesion type of the lesion area in the to-be-annotated medical image are not correct.

In some embodiments, the third annotation unit is further configured to: form a pre-split area in the lesion area of the to-be-annotated medical image using the lesion area splitting model, and output the pre-split area to a client terminal, to enable a user to slightly adjust the pre-split area; and receive and save the pre-split area slightly adjusted by the user.

In some embodiments, the apparatus further includes: an image classification model retraining unit configured to add the to-be-annotated medical image and the classification information of the to-be-annotated medical image to the first medical image training set to retrain the image classification model.

In some embodiments, the apparatus further includes: a lesion area detection model retraining unit configured to add the to-be-annotated medical image, and the annotated lesion area and the lesion type of the lesion area in the to-be-annotated medical image to the second medical image training set to retrain the lesion area detection model.

In some embodiments, the apparatus further includes: a lesion area splitting model retraining unit configured to add the to-be-annotated medical image with the framed lesion area and the split image of the to-be-annotated medical image to the third medical image training set to retrain the lesion area splitting model.

The method and apparatus for annotating a medical image provided by the embodiments of the present disclosure may annotate classification information for an acquired to-be-annotated medical image, frame a lesion area in the to-be-annotated medical image and annotate a lesion type of the lesion area using a pre-trained lesion area detection model, and then obtain a split image of the framed lesion area by splitting the to-be-annotated medical image with the framed lesion area, thereby achieving automatically annotating a to-be-annotated medical image using a pre-trained model at reduced labor and time cost.

BRIEF DESCRIPTION OF THE DRAWINGS

By reading and referring to detailed description on the non-limiting embodiments in the following accompanying drawings, other features, objects and advantages of the present disclosure will become more apparent.

DETAILED DESCRIPTION OF EMBODIMENTS

The present disclosure will be further described below in detail in combination with the accompanying drawings and the embodiments. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the embodiments in the present disclosure and the features in the embodiments may be combined with each other on a non-conflict basis. The present disclosure will be described below in detail with reference to the accompanying drawings and in combination with the embodiments.

Figure 1:
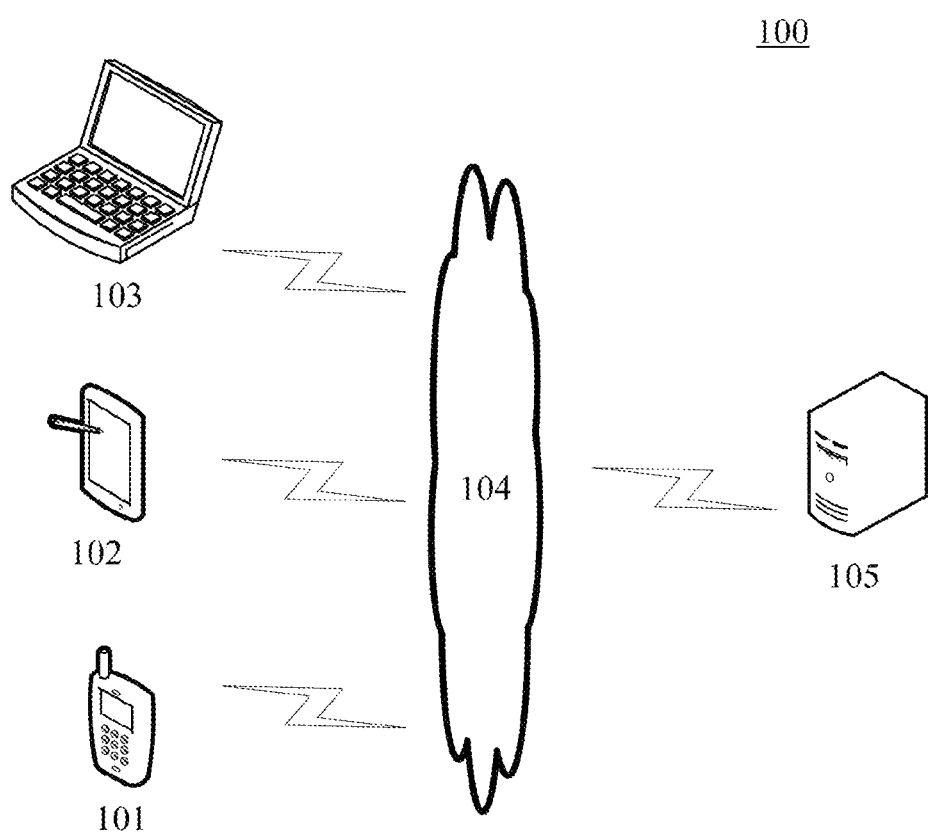
FIG. 1 is an architectural diagram of an exemplary system in which the present disclosure may be implemented.

FIG. 1 shows an exemplary architecture of a system 100 which may be used by a method for annotating a medical image or an apparatus for annotating a medical image according to the embodiments of the present disclosure.

As shown in FIG. 1, the system architecture 100 may include terminal devices 101, 102 and 103, a network 104 and a server 105. The network 104 serves as a medium providing a communication link between the terminal devices 101, 102 and 103 and the server 105. The network 104 may include various types of connections, such as wired or wireless transmission links, or optical fibers.

The user 110 may use the terminal devices 101, 102 and 103 to interact with the server 105 through the network 104, in order to receive or transmit medical images, etc. Various communication client applications, such as web browser applications, image viewing software, image processing software, instant messaging tools, mailbox clients, and social platform software may be installed on the terminal devices 101, 102 and 103.

The terminal devices 101, 102 and 103 may be various electronic devices having display screens and supporting image viewing, including but not limited to, smart phones, tablet computers, e-book readers, MP3 (Moving Picture Experts Group Audio Layer III) players, MP4 (Moving Picture Experts Group Audio Layer IV) players, laptop computers and desktop computers.

The server 105 may be a server providing various services, for example, a backend image server that supports for medical images displayed on the terminal devices 101, 102 or 103. The backend image server may perform annotation processing including splitting and classification on received medical images, and return a processing result (for example, a result of image split) to the terminal devices 101, 102 and 103.

It should be noted that the method for annotating a medical image according to the embodiments of the present disclosure is generally executed by the server 105. Accordingly, an apparatus for annotating a medical image is generally installed on the server 105.

It should be appreciated that the numbers of the terminal devices, the networks and the servers in FIG. 1 are merely illustrative. Any number of terminal devices, networks and servers may be provided based on the actual requirements.

Figure 2:
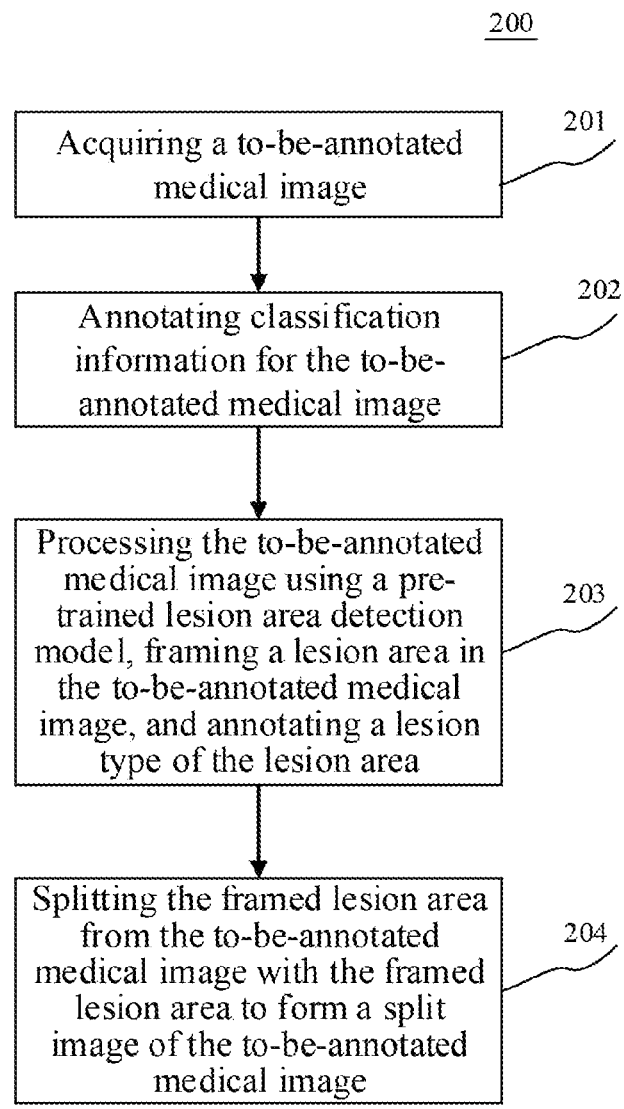
FIG. 2 is a flowchart of an embodiment of a method for annotating a medical image according to the present disclosure.

By further referring to FIG. 2, a flow 200 of an embodiment of a method for annotating a medical image according to the present disclosure is shown. The method for annotating a medical image includes the following steps.

Step 201: acquiring a to-be-annotated medical image.

In this embodiment, an electronic device (e.g., the server as shown in FIG. 1) on which the method for annotating a medical image is performed may receive one or more to-be-annotated medical images from a terminal used by a user to view and save a medical image, by way of a wired connection or a wireless connection. Here, the to-be-annotated medical image may be a medical image, such as a fundus image and a lung CT image, acquired by various methods, such as photography, Computed Tomography (CT) and Magnetic Resonance Imaging (MRI). It should be noted that the wireless connection type may include, but is not limited to, 3G/4G connection, WiFi connection, Bluetooth connection, WiMAX connection, Zigbee connection, ultra wideband (UWB) connection, and other wireless connections that are known at present or are to be developed in the future.

Step 202: annotating classification information for the to-be-annotated medical image.

In the embodiment, based on the one or more to-be-annotated medical images acquired in the step 201, the electronic device may annotate classification information for the to-be-annotated medical images. Specifically, the electronic device may annotate classification information for each of the to-be-annotated medical images based on a received operation instruction sent by a user via a terminal device, or automatically annotate classification information for each of the to-be-annotated medical images using a pre-trained model, or the like. It should be noted that the respective medical images usually may have different categories of diagnostic results, and diagnostic results of some categories may also correspond to different grades. Therefore, the classification information may include a category of a diagnosis result and a grade of the diagnosis result corresponding to the medical image. For example, if a medical image is a lung CT, then the category of the diagnosis result corresponding to the medical image may be a benign tumor, a malignant tumor, a pulmonary nodule, no pathological change, or the like, where the malignant tumor may further include three grades: early, middle and late stages; and if a medical image is a fundus image, then the category of the diagnosis result corresponding to the medical image may be diabetic retinopathy, no pathological change, or the like, where the diabetic retinopathy may include four grades: 1-4.

Step 203: processing the to-be-annotated medical image using a pre-trained lesion area detection model, framing a lesion area in the to-be-annotated medical image, and annotating a lesion type of the lesion area.

In the embodiment, the electronic device may pre-train a lesion area detection model. The pre-trained lesion area detection model may first be used for detecting each area of an inputted medical image, so as to detect a possibly existing lesion area from the medical image, framing the lesion area in the medical image based on a position of the detected lesion area and a size of the lesion area, and then annotating the lesion type of the framed lesion area. Therefore, the electronic device may input the to-be-annotated medical image into the lesion area detection model, the lesion area detection model may output the to-be-annotated medical image with the framed lesion area, and may annotate a corresponding lesion type for the framed lesion area, thereby achieving automatically annotating a position, size and lesion type of the lesion area for a to-be-annotated medical image, avoiding the phenomenon that a doctor needs to annotate each medical image after viewing and analyzing the each medical image, and effectively reducing the time for annotating the medical image.

Usually, there may be only one lesion area in a to-be-annotated medical image, and there may also be only one lesion type in the lesion area. Under this circumstance, the lesion area detection model may frame the lesion area in the to-be-annotated medical image, and annotate the lesion area with the corresponding lesion type. Or, there may also be a plurality of lesion areas in a to-be-annotated medical image, and there may be one or more lesion types in each of the lesion areas. Under this circumstance, the lesion area detection model may frame each of the lesion areas in the to-be-annotated medical image, and annotate each of the lesion areas with corresponding lesion types thereof.

Step 204: splitting the framed lesion area from the to-be-annotated medical image with the framed lesion area to form a split image of the to-be-annotated medical image.

In this embodiment, based on the to-be-annotated medical image with the framed lesion area acquired in the step 203, the electronic device may split the framed lesion area from the to-be-annotated medical image with the framed lesion area by a variety of means to form a split image of the to-be-annotated medical image, so that the to-be-annotated medical image may be annotated with a split image. As an example, the user may split the to-be-annotated medical image by way of manual operation, and generate a split image of the lesion area. Under this circumstance, the electronic device may receive an operation instruction sent by a user via a terminal device, and split the framed lesion area from the non-lesion area in the to-be-annotated medical image to acquire a split image of the lesion area of the to-be-annotated medical image. Or, the electronic device may also automatically split the to-be-annotated medical image with the framed lesion area using an image splitting algorithm to acquire a split image of the framed lesion area therein.

Usually, after annotation of the to-be-annotated medical image is completed, it is still necessary to check the annotated medical image by a crowd testing platform or the like. The method for annotating a medical image provided by the embodiment may split the lesion area from the non-lesion area in a to-be-annotated medical image, so that the staff of the crowd testing platform or the like may, when checking annotated information of the to-be-annotated medical image, only pay attention to the split lesion area, thereby effectively reducing annotation errors caused by less medical background knowledge of the staff of the crowd testing platform or the like, and improving the work efficiency of the staff.

The method 200 for annotating a medical image provided by the embodiments of the present disclosure may annotate classification information for an acquired to-be-annotated medical image, frame a lesion area in the to-be-annotated medical image and annotate a lesion type of the lesion area using a pre-trained lesion area detection model, and then obtain a split image of the framed lesion area by splitting the to-be-annotated medical image with the framed lesion area, thereby achieving automatically annotating a to-be-annotated medical image using a pre-trained model at reduced labor and time cost.

Figure 3:
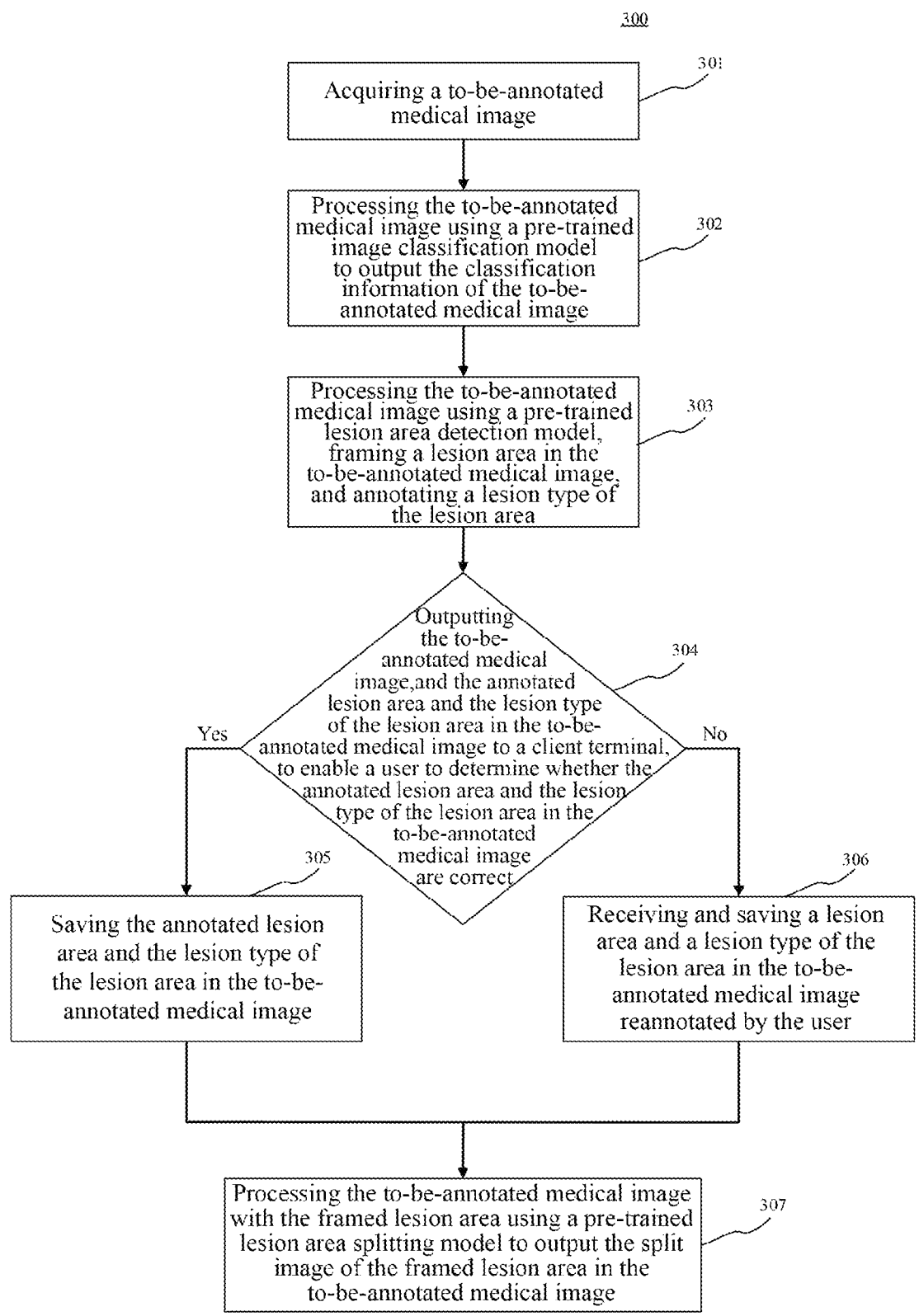
FIG. 3 is a flowchart of another embodiment of a method for annotating a medical image according to the present disclosure.

By further referring to FIG. 3, a flow 300 of another embodiment of a method for annotating a medical image according to the present disclosure is shown. As shown in FIG. 3, the method for annotating a medical image according to the embodiment may include the following steps:

Step 301: acquiring a to-be-annotated medical image.

In this embodiment, an electronic device (e.g., the server as shown in FIG. 1) on which the method for annotating a medical image is performed may receive one or more to-be-annotated medical images from a terminal used by a user to view and save a medical image, by way of a wired connection or a wireless connection. Here, the to-be-annotated medical image may be a medical image, such as a fundus image and a lung CT image, acquired by the methods, such as photography, Computed Tomography (CT) and Magnetic Resonance Imaging (MRI).

Step 302: processing the to-be-annotated medical image using a pre-trained image classification model to output the classification information of the to-be-annotated medical image.

In the embodiment, the electronic device may pre-train an image classification model for annotating classification information for a medical image, and the image classification model may output, in response to an inputted to-be-annotated medical image, classification information of the to-be-annotated medical image. Therefore, based on the to-be-annotated medical image acquired in the step 301, the electronic device may input the to-be-annotated medical image into the pre-trained image classification model, and the image classification model may output classification information of the to-be-annotated medical image. The classification information may include a category of a diagnosis result and a grade of the diagnosis result of the medical image. It can be seen that the image classification model may classify and grade a medical image inputted thereinto.

In some optional implementations of the embodiment, a considerable amount of annotated medical images may be used as training samples for training the image classification model. Specifically, first, a first medical image training set may be acquired as training samples, the first medical image training set may include a considerable amount of medical images, each of the medical images in the first medical image training set is annotated with classification information, and then the image classification model may be trained using a convolutional neural network (e.g., VGGNet, ResNet, etc.) suitable for classification, using the medical images in the first medical image training set as inputted training samples of the image classification model, and using the classification information annotated on each of the medical images as outputted training samples.

In some optional implementations of the embodiment, when annotation of the to-be-annotated medical image with the classification information is completed, the to-be-annotated medical image and the annotated classification information thereof may be added to the first medical image training set as training samples, to enable the electronic device to retrain the image classification model using the first medical image training set containing the to-be-annotated medical image and the classification information of the to-be-annotated medical image. The method may improve the accuracy in annotating classification information for a medial image by an image classification model.

Step 303: processing the to-be-annotated medical image using a pre-trained lesion area detection model, framing a lesion area in the to-be-annotated medical image, and annotating a lesion type of the lesion area.

In the embodiment, the electronic device may pre-train a lesion area detection model. The pre-trained lesion area detection model may first be used for detecting each area of an inputted medical image, so as to detect a possibly existing lesion area from the medical image, framing the lesion area in the medical image based on a position and size of the detected lesion area, and then annotating the lesion type of the framed lesion area. Therefore, the electronic device may input the to-be-annotated medical image into the lesion area detection model, the lesion area detection model may output the to-be-annotated medical image with the framed lesion area, and may annotate the framed lesion area with a corresponding lesion type, thereby achieving automatically annotating a position, size and lesion type of the lesion area for a to-be-annotated medical image, avoiding the phenomenon that a doctor needs to annotate each medical image after viewing and analyzing the each medical image, and effectively reducing the time for annotating the medical image.

In some optional implementations of the embodiment, a considerable amount of annotated medical images may be used as training samples for training the lesion area detection model. Specifically, first, a second medical image training set may be acquired as training samples, and the second medical image training set may include a considerable amount of medical images, the medical images in the second medical image training set are annotated with lesion areas and lesion types of the lesion areas, and then the lesion area detection model may be trained using a convolutional neural network (e.g., Faster RCNN, Mask R-CNN, etc.) suitable for lesion area detection, using the medical images in the second medical image training set as inputted training samples of the lesion area detection model, and using the annotated lesion area and the lesion type of the lesion area corresponding to each of the medical images as outputted training samples.

Step 304: outputting the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct.

In the embodiment, based on the lesion area and the lesion type of the lesion area annotated in the step 303, the electronic device may output the to-be-annotated medical image, and the lesion area and the lesion type of the lesion area annotated in the to-be-annotated medical image to a client terminal, to enable the user to view whether the framed lesion area in the to-be-annotated medical image and the annotated lesion type of the lesion area are correct via a terminal device of the client terminal. Optionally, while outputting the to-be-annotated medical image, and the lesion area and the lesion type of the lesion area annotated in the to-be-annotated medical image to a client terminal, the electronic device may further output classification information of the to-be-annotated medical image to the client terminal. Under this circumstance, the user may supplement the to-be-annotated medical image with classification information, and judge the framed lesion area therein and the lesion type of the lesion area, to determine whether the framed lesion area in the to-be-annotated medical image and the annotated lesion type of the lesion area are correct. This method may further improve the user determination efficiency and accuracy. When the user determines that the framed lesion area in the to-be-annotated medical image and the annotated lesion type of the lesion area are correct, step 305 may be performed. Otherwise, step 306 may be performed.

Step 305: saving the annotated lesion area and the lesion type of the lesion area in the to-be-annotated medical image.

In the embodiment, based on the situation that the framed lesion area and the annotated lesion type of the lesion area in the to-be-annotated medical image are correct, as determined in the step 304, the electronic device may save the framed lesion area and the annotated lesion type of the lesion area in the to-be-annotated medical image, i.e., the electronic device may save the lesion area and the lesion type of the lesion area annotated in the to-be-annotated medical image.

Step 306: receiving and saving a lesion area and a lesion type of the lesion area in the to-be-annotated medical image reannotated by the user.

In the embodiment, based on the situation that the framed lesion area in the to-be-annotated medical image and the annotated lesion type of the lesion area are not correct, as determined in the step 304, for example, the framed lesion area in the to-be-annotated medical image is not a lesion area, or the annotated lesion type of the lesion area is not correct, then the user may reannotate the incorrect contents, and the electronic device may receive and save a lesion area and a lesion type of the lesion area in the to-be-annotated medical image reannotated by the user. The method may improve not only the efficiency in annotating medical images, but also the accuracy in annotating medical images.

Usually, when receiving the annotated information of the to-be-annotated medical image outputted by the electronic device, the client terminal may present the lesion area and the lesion type of the lesion area annotated in the to-be-annotated medical image to the user via a terminal device. Here, the annotated information of the to-be-annotated medical image may be the lesion area and the lesion type corresponding to the lesion area annotated in the to-be-annotated medical image. Furthermore, the client terminal may further provide a user with a dialogue box displaying "Yes" and "No", so that the user may click "Yes" when determining that the annotated information of the to-be-annotated medical image is correct, or click "No" when determining that the annotated information of the to-be-annotated medical image is not correct. After clicking "No", the user may manually correct incorrectly annotated information of the to-be-annotated medical image, and send the corrected annotated information to the electronic device, so that the electronic device may receive and save the corrected annotated information.

In some optional implementations of the embodiment, when annotation of the to-be-annotated medical image with the lesion area and the lesion type of the lesion area is completed, the to-be-annotated medical image, and the annotated lesion area and the lesion type of the lesion area thereof may be added to the second medical image training set as training samples, to enable the electronic device to retrain the lesion area detection model using the second medical image training set containing the to-be-annotated medical image, and the lesion area and the lesion type of the lesion area of the to-be-annotated medical image. The method may improve the accuracy in annotating a medial image with the lesion area and the lesion type of the lesion area by a lesion area detection model.

Step 307: processing the to-be-annotated medical image with the framed lesion area using a pre-trained lesion area splitting model to output the split image of the framed lesion area in the to-be-annotated medical image.

In the embodiment, the electronic device may pre-train a lesion area splitting model for obtaining a split image of a framed lesion area by splitting the medical image with the framed lesion area. The lesion area splitting model may split, in response to an inputted medical image with a framed lesion area, the framed lesion area in the medical image, and output the split image after splitting the medical image. Therefore, when acquiring the to-be-annotated medical image with the framed lesion area, the electronic device may input the to-be-annotated medical image with the framed lesion area into the lesion area splitting model, and the lesion area splitting model may output the split image of the framed lesion area in the to-be-annotated medical image. It can be seen that the lesion area splitting model may split the lesion area and the non-lesion area of the to-be-annotated medical image, and annotate a split image for the to-be-annotated medical image.

In some optional implementations of the embodiment, a considerable amount of annotated medical images may be used as training samples for training the lesion area splitting model. Specifically, first, a third medical image training set may be acquired as training samples, the third medical image training set may include a considerable amount of medical images with framed lesion areas, the medical images with the framed lesion areas in the third medical training set are annotated with the split image of the framed lesion areas, and then the lesion area splitting model may be trained using a convolutional neural network (e.g., FCN, U-Net, etc.) suitable for image splitting, using the medical images with the framed lesion areas in the third medical image training set as inputted training samples of the lesion area splitting model, and using the split image of the lesion areas obtained by splitting each of the medical images with the framed lesion areas as outputted training samples.

In some optional implementations of the embodiment, in order to improve the accuracy of the split image of the split lesion area of the to-be-annotated medical image, the to-be-annotated medial image may be further slightly manually adjusted before splitting. Therefore, before image splitting of the inputted to-be-annotated medial image with the framed lesion area, the lesion area splitting model may pre-form a pre-split area on the to-be-annotated medial image, and output the pre-split area to a client terminal. The terminal device of the client terminal may display the pre-split area in the to-be-annotated medial image to the user. The user may slightly adjust the pre-split area by observing the pixel information, such as image gray scale and color change, of the medical image displayed on the terminal device, so as to accurately form the pre-split area in the lesion area on the to-be-annotated medial image. The electronic device may acquire the pre-split area slightly adjusted by the user from the client terminal, and save the pre-split area, so that the lesion area splitting model may accurately split the lesion area and the non-lesion area in the to-be-annotated medial image based on the slightly adjusted pre-split area, and improve the accuracy of the annotated split image of the to-be-annotated medial image.

In some optional implementations of the embodiment, when the to-be-annotated medical image is annotated with the split image of the lesion area, the to-be-annotated medical image and the annotated split image may be added to the third medical image training set as training samples, to enable the electronic device to retrain the lesion area splitting model using the third medical image training set containing the to-be-annotated medical image and the split image of the to-be-annotated medical image. This method may improve the accuracy in splitting an image by the lesion area splitting model.

In some optional implementations of the embodiment, the first medical image training set, the second medical image training set and the third medical image training set may be a same medical image training set, and a plurality of medical images in the medical image training set may be annotated with classification information, lesion areas, lesion types of the lesion areas and split images. Under this circumstance, the image classification model, the lesion area detection model and the lesion area splitting model may be trained using the medical image training set.

As can be seen from FIG. 3, compared with the embodiment corresponding to FIG. 2, the flow 300 of a method for annotating a medical image according to the embodiment highlights annotating classification information for a to-be-annotated medical image using an image classification model and annotating a split image for a to-be-annotated medical image using a lesion area splitting model. Accordingly, the solution described in the embodiment may automatically annotate classification information and a split image for a medical image, thereby further improving the efficiency in medical image annotation.

Figure 4:
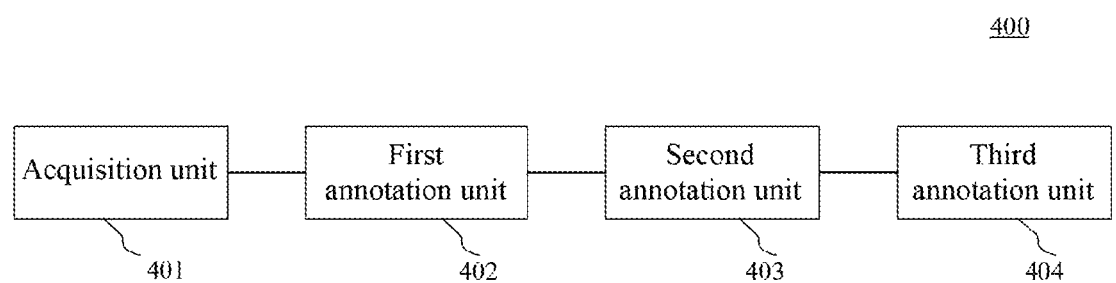
FIG. 4 is a structural schematic diagram of an embodiment of an apparatus for annotating a medical image according to the present disclosure.

By further referring to FIG. 4, as implementations of the methods shown in the above figures, the present disclosure provides an embodiment of an apparatus for annotating a medical image. The embodiment of the apparatus corresponds to the embodiment of the method shown in FIG. 2, and the apparatus may be specifically applied to a variety of electronic devices.

As shown in FIG. 4, the apparatus 400 for annotating a medical image according to the embodiment includes an acquisition unit 401, a first annotation unit 402, a second annotation unit 403 and a third annotation unit 404. The acquisition unit 401 is configured to acquire a to-be-annotated medical image; the first annotation unit 402 is configured to annotate classification information for the to-be-annotated medical image, wherein the classification information includes a category of a diagnosis result and a grade of the diagnosis result corresponding to the medical image; the second annotation unit 403 is configured to process the to-be-annotated medical image using a pre-trained lesion area detection model, frame a lesion area in the to-be-annotated medical image, and annotate a lesion type of the lesion area, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and the third annotation unit 404 is configured to split the framed lesion area from the to-be-annotated medical image with the framed lesion area to form a split image of the to-be-annotated medical image, to enable the to-be-annotated medical image to be annotated with the split image.

In some optional implementations of the embodiment, the first annotation unit 402 is further configured to: process the to-be-annotated medical image using a pre-trained image classification model to output the classification information of the to-be-annotated medical image, wherein the image classification model is used for annotating a category of a diagnosis result and a grade of the diagnosis result for the medical image.

In some optional implementations of the embodiment, the third annotation unit 404 is further configured to: process the to-be-annotated medical image with the framed lesion area using a pre-trained lesion area splitting model to output the split image of the framed lesion area in the to-be-annotated medical image, wherein the lesion area splitting model is used for obtaining the split image of the lesion area by splitting the medical image with the framed lesion area.

In some optional implementations of the embodiment, the apparatus 400 further includes an image classification model training unit. The image classification model training unit includes: a first acquisition module configured to acquire a first medical image training set, the first medical image training set including a plurality of medical images and the classification information annotated on each of the medical images; and a first training module configured to obtain the image classification model by training, using a convolutional neural network based on the first medical image training set.

In some optional implementations of the embodiment, the apparatus 400 further includes a lesion area detection model training unit. The lesion area detection model training unit includes a second acquisition module configured to acquire a second medical image training set, the second medical image training set including a plurality of medical images, and lesion areas and lesion types of the lesion areas annotated on each of the medical images; and a second training unit configured to obtain the lesion area detection model by training, using a convolutional neural network based on the second medical image training set.

In some optional implementations of the embodiment, the apparatus 400 further includes a lesion area splitting model training unit. The lesion area splitting model training unit includes: a third acquisition module configured to acquire a third medical image training set, the third medical image training set including a plurality of medical images with framed lesion areas and a split image of the lesion areas of the medical images with the framed lesion areas; and a third training module configured to obtain the lesion area splitting model by training, using a convolutional neural network based on the third medical image training set.

In some optional implementations of the embodiment, the second annotation unit 403 is further configured to: output the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct; and save the annotated lesion area and the lesion type of the lesion area in the to-be-annotated medical image, if the annotated lesion area and the lesion type of the lesion area in the to-be-annotated medical image are correct; or receive and save a lesion area and a lesion type of the lesion area in the to-be-annotated medical image re-annotated by the user, if the annotated lesion area and the lesion type of the lesion area in the to-be-annotated medical image are not correct.

In some optional implementations of the embodiment, the third annotation unit 404 is further configured to: form a pre-split area in the lesion area of the to-be-annotated medical image using the lesion area splitting model, and output the pre-split area to a client terminal, to enable a user to slightly adjust the pre-split area; and receive and save the pre-split area slightly adjusted by the user.

In some optional implementations of the embodiment, the apparatus 400 further includes: an image classification model retraining unit configured to add the to-be-annotated medical image and the classification information of the to-be-annotated medical image to the first medical image training set to retrain the image classification model.

In some optional implementations of the embodiment, the apparatus 400 further includes: a lesion area detection model retraining unit configured to add the to-be-annotated medical image, and the annotated lesion area and the lesion type of the lesion area in the to-be-annotated medical image to the second medical image training set to retrain the lesion area detection model.

In some optional implementations of the embodiment, the apparatus 400 further includes: a lesion area splitting model retraining unit configured to add the to-be-annotated medical image with the framed lesion area and the split image of the to-be-annotated medical image to the third medical image training set to retrain the lesion area splitting model.

Figure 5:
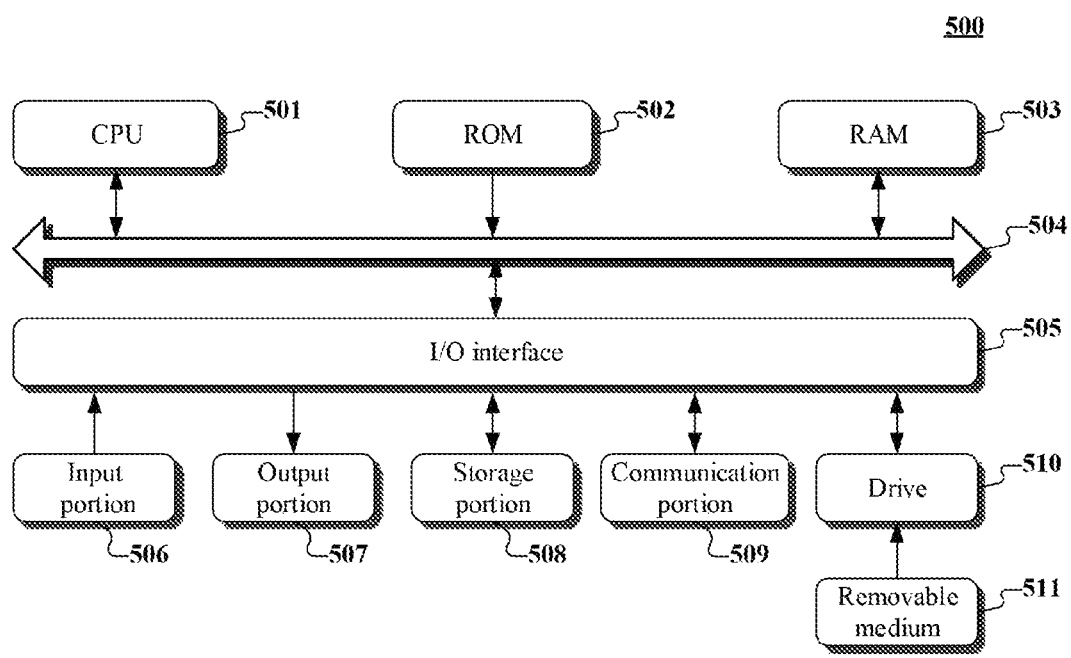
FIG. 5 is a structural schematic diagram of a computer system adapted to implement a terminal device or a server according to an embodiment of the present disclosure.

Referring to FIG. 5, a schematic structural diagram of a computer system 500 adapted to implement a terminal device/server of the embodiments of the present disclosure is shown. The terminal device/server shown in FIG. 5 is merely an example, but does not impose any restrictions on the function and scope of embodiments of the present disclosure.

As shown in FIG. 5, the computer system 500 includes a central processing unit (CPU) 501, which may execute various appropriate actions and processes in accordance with a program stored in a read-only memory (ROM) 502 or a program loaded into a random access memory (RAM) 503 from a storage portion 508. The RAM 503 also stores various programs and data required by operations of the system 500. The CPU 501, the ROM 502 and the RAM 503 are connected to each other through a bus 504. An input/output (I/O) interface 505 is also connected to the bus 504.

The following components are connected to the I/O interface 505: an input portion 506 including a keyboard, a mouse etc.; an output portion 507 comprising a cathode ray tube (CRT), a liquid crystal display device (LCD), a speaker etc.; a storage portion 508 including a hard disk and the like; and a communication portion 509 comprising a network interface card, such as a LAN card and a modem. The communication portion 509 performs communication processes via a network, such as the Internet. A driver 510 is also connected to the I/O interface 505 as required. A removable medium 511, such as a magnetic disk, an optical disk, a magneto-optical disk, and a semiconductor memory, may be installed on the driver 510, to facilitate the retrieval of a computer program from the removable medium 511, and the installation thereof on the storage portion 508 as needed.

In particular, according to embodiments of the present disclosure, the process described above with reference to the flow chart may be implemented in a computer software program. For example, an embodiment of the present disclosure includes a computer program product, which comprises a computer program that is tangibly embedded in a machine-readable medium. The computer program comprises program codes for executing the method as illustrated in the flow chart. In such an embodiment, the computer program may be downloaded and installed from a network via the communication portion 509, and/or may be installed from the removable media 511. The computer program, when executed by the central processing unit (CPU) 501, implements the above mentioned functionalities as defined by the methods of the present disclosure. It should be noted that the computer readable medium in the present disclosure may be computer readable signal medium or computer readable storage medium or any combination of the above two. An example of the computer readable storage medium may include, but not limited to: electric, magnetic, optical, electromagnetic, infrared, or semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. In the present disclosure, the computer readable signal medium may include data signal in the base band or propagating as parts of a carrier, in which computer readable program codes are carried. The propagating signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units involved in the embodiments of the present disclosure may be implemented by means of software or hardware. The described units may also be provided in a processor, for example, described as: a processor, comprising an acquisition unit, a first annotation unit, a second annotation unit, and a third annotation unit, where the names of these units do not in some cases constitute a limitation to such units themselves. For example, the acquisition unit may also be described as "a unit for acquiring a to-be-annotated medical image."

In another aspect, the present disclosure further provides a computer-readable storage medium. The computer-readable storage medium may be the computer storage medium included in the apparatus in the above described embodiments, or a stand-alone computer-readable storage medium not assembled into the apparatus. The computer-readable storage medium stores one or more programs. The one or more programs, when executed by the apparatus, cause the apparatus to: acquiring a to-be-annotated medical image; annotating classification information for the to-be-annotated medical image, wherein the classification information comprises a category of a diagnosis result and a grade of the diagnosis result corresponding to the medical image; processing the to-be-annotated medical image using a pre-trained lesion area detection model, framing a lesion area in the to-be-annotated medical image, and annotating a lesion type of the lesion area, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and splitting the framed lesion area from the to-be-annotated medical image with the framed lesion area to form a split image of the to-be-annotated medical image, to enable the to-be-annotated medical image to be annotated with the split image.

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the disclosure. Technical schemes formed by the above-described features being interchanged with, but not limited to, technical features with similar functions disclosed in the present disclosure are examples.

What is claimed is:

1. A method for annotating a medical image, comprising:
acquiring a to-be-annotated medical image;
annotating classification information for the to-be-annotated medical image, wherein the classification information comprises a category of a diagnosis result and a grade of the diagnosis result corresponding to the medical image;
processing the to-be-annotated medical image using a pre-trained lesion area detection model, framing a lesion area in the to-be-annotated medical image, and annotating a lesion type of the framed lesion area in the to-be-annotated medical image, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and
splitting the framed lesion area from the to-be-annotated medical image with the framed lesion area to form a split image of the framed lesion area in the to-be-annotated medical image, to enable the to-be-annotated medical image to be annotated with the split image.

2. The method according to claim 1, wherein the annotating classification information for the to-be-annotated medical image comprises:
processing the to-be-annotated medical image using a pre-trained image classification model to output the classification information of the to-be-annotated medical image, wherein the image classification model is used for annotating the classification information for the medical image.

3. The method according to claim 1, wherein the splitting the framed lesion area from the to-be-annotated medical image with the framed lesion area to form a split image of the to-be-annotated medical image comprises:
processing the to-be-annotated medical image with the framed lesion area using a pre-trained lesion area splitting model to output the split image of the framed lesion area in the to-be-annotated medical image, wherein the lesion area splitting model is used for obtaining the split image of the lesion area by splitting the medical image with the framed lesion area.

4. The method according to claim 2, further comprising training the image classification model; wherein
the training the image classification model comprises:
acquiring a first medical image training set, the first medical image training set comprising a plurality of medical images and the classification information annotated on each of the medical images; and
obtaining the image classification model by training, using a convolutional neural network based on the first medical image training set.

5. The method according to claim 1, further comprising training the lesion area detection model; wherein
the training the lesion area detection model comprises:
acquiring a second medical image training set, the second medical image training set comprising a plurality of medical images, lesion areas and lesion types of the lesion areas annotated on each of the medical images; and
obtaining the lesion area detection model by training, using a convolutional neural network based on the second medical image training set.

6. The method according to claim 3, further comprising training the lesion area splitting model; wherein
the training the lesion area splitting model comprises:
acquiring a third medical image training set, the third medical image training set comprising a plurality of medical images with framed lesion areas and a split image of the lesion areas of the medical images with the framed lesion areas; and
obtaining the lesion area splitting model by training, using a convolutional neural network based on the third medical image training set.

7. The method according to claim 1, wherein after the processing the to-be-annotated medical image using a pre-trained lesion area detection model, framing a lesion area in the to-be-annotated medical image, and annotating the lesion type of the lesion area, the method further comprises:
outputting the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct; and
saving the annotated lesion area and the lesion type of the lesion area in the to-be-annotated medical image, if the annotated lesion area and the lesion type of the lesion area in the to-be-annotated medical image are correct; or
receiving and saving a lesion area and a lesion type of the lesion area in the to-be-annotated medical image reannotated by the user, if the annotated lesion area and the lesion type of the lesion area in the to-be-annotated medical image are not correct.

8. The method according to claim 3, wherein before the outputting the split image of the framed lesion area in the to-be-annotated medical image, the method further comprises:
forming a pre-split area in the lesion area of the to-be-annotated medical image using the lesion area splitting model, and outputting the pre-split area to a client terminal, to enable a user to slightly adjust the pre-split area; and
receiving and saving the pre-split area slightly adjusted by the user.

9. The method according to claim 4, further comprising:
adding the to-be-annotated medical image and the classification information of the to-be-annotated medical image to the first medical image training set to retrain the image classification model.

10. The method according to claim 5, further comprising:
adding the to-be-annotated medical image, the annotated lesion area and the lesion type of the lesion area in the to-be-annotated medical image to the second medical image training set to retrain the lesion area detection model.

11. The method according to claim 6, further comprising:
adding the to-be-annotated medical image with the framed lesion area and the split image of the to-be-annotated medical image to the third medical image training set to retrain the lesion area splitting model.

12. An apparatus for annotating a medical image, comprising: at least one processor; and
a memory storing instructions, the instructions when executed by the at least one processor, cause the at least one processor to perform operations, the operations comprising:
acquiring a to-be-annotated medical image;
annotating classification information for the to-be-annotated medical image, wherein the classification information comprises a category of a diagnosis result and a grade of the diagnosis result corresponding to the medical image;
processing the to-be-annotated medical image using a pre-trained lesion area detection model, framing a lesion area in the to-be-annotated medical image, and annotating a lesion type of the framed lesion area in the to-be-annotated medical image, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and
splitting the framed lesion area from the to-be-annotated medical image with the framed lesion area to form a split image of the framed lesion area in the to-be-annotated medical image, to enable the to-be-annotated medical image to be annotated with the split image.

13. The apparatus according to claim 12, wherein the annotating classification information for the to-be-annotated medical image comprises:

processing the to-be-annotated medical image using a pre-trained image classification model to output the classification information of the to-be-annotated medical image, wherein the image classification model is used for annotating a category of a diagnosis result and a grade of the diagnosis result for the medical image.

14. The apparatus according to claim 12, wherein the splitting the framed lesion area from the to-be-annotated medical image with the framed lesion area to form a split image of the to-be-annotated medical image comprises:
processing the to-be-annotated medical image with the framed lesion area using a pre-trained lesion area splitting model to output the split image of the framed lesion area in the to-be-annotated medical image, wherein the lesion area splitting model is used for obtaining the split image of the lesion area by splitting the medical image with the framed lesion area.

15. The apparatus according to claim 13, the operations further comprise training the image classification model; wherein
the training the image classification model comprises:
acquiring a first medical image training set, the first medical image training set comprising a plurality of medical images and the classification information annotated on each of the medical images; and
obtaining the image classification model by training, using a convolutional neural network based on the first medical image training set.

16. The apparatus according to claim 12, the operations further comprise training the lesion area detection model; wherein
the training the lesion area detection model comprises:
acquiring a second medical image training set, the second medical image training set comprising a plurality of medical images, lesion areas and lesion types of the lesion areas annotated on each of the medical images; and
obtaining the lesion area detection model by training, using a convolutional neural network based on the second medical image training set.

17. The apparatus according to claim 14, the operations further comprise training the lesion area splitting model; wherein
the training the lesion area splitting model comprises:
acquiring a third medical image training set, the third medical image training set comprising a plurality of medical images with framed lesion areas and a split image of the lesion areas of the medical images with the framed lesion areas; and
obtaining the lesion area splitting model by training, using a convolutional neural network based on the third medical image training set.

18. The apparatus according to claim 12, wherein after the processing the to-be-annotated medical image using a pre-trained lesion area detection model, framing a lesion area in the to-be-annotated medical image, and annotating the lesion type of the lesion area, the operations further comprise:
outputting the to-be-annotated medical image, and the annotated lesion area and the lesion type of the lesion area in the to-be-annotated medical image to a client terminal, to enable a user to determine whether the annotated lesion area and the lesion type of the lesion area in the to-be-annotated medical image are correct; and
saving the annotated lesion area and the lesion type of the lesion area in the to-be-annotated medical image, if the annotated lesion area and the lesion type of the lesion area in the to-be-annotated medical image are correct; or
receiving and saving a lesion area and a lesion type of the lesion area in the to-be-annotated medical image reannotated by the user, if the annotated lesion area and the lesion type of the lesion area in the to-be-annotated medical image are not correct.

19. The apparatus according to claim 14, wherein before the outputting the split image of the framed lesion area in the to-be-annotated medical image, the operations further comprise:
forming a pre-split area in the lesion area of the to-be-annotated medical image using the lesion area splitting model, and outputting the pre-split area to a client terminal, to enable a user to slightly adjust the pre-split area; and
receiving and saving the pre-split area slightly adjusted by the user.

20. The apparatus according to claim 15, the operations further comprise:
adding the to-be-annotated medical image and the classification information of the to-be-annotated medical image to the first medical image training set to retrain the image classification model.

21. The apparatus according to claim 16, the operations further comprise:
adding the to-be-annotated medical image, the annotated lesion area and the lesion type of the lesion area in the to-be-annotated medical image to the second medical image training set to retrain the lesion area detection model.

22. The apparatus according to claim 17, the operations further comprise:
adding the to-be-annotated medical image with the framed lesion area and the split image of the to-be-annotated medical image to the third medical image training set to retrain the lesion area splitting model.

23. A non-transitory computer storage medium storing a computer program, the computer program when executed by one or more processors, causes the one or more processors to perform operations, the operations comprising:
acquiring a to-be-annotated medical image;
annotating classification information for the to-be-annotated medical image, wherein the classification information comprises a category of a diagnosis result and a grade of the diagnosis result corresponding to the medical image;
processing the to-be-annotated medical image using a pre-trained lesion area detection model, framing a lesion area in the to-be-annotated medical image, and annotating a lesion type of the framed lesion area in the to-be-annotated medical image, to enable the to-be-annotated medical image to be annotated with the lesion area and the lesion type of the lesion area, wherein the lesion area detection model is used for framing the lesion area based on a position and size of the lesion area identified in the medical image, and annotating the lesion type of the lesion area; and
splitting the framed lesion area from the to-be-annotated medical image with the framed lesion area to form a split image of the framed lesion area in the to-be-annotated medical image, to enable the to-be-annotated medical image to be annotated with the split image.

* * * * *